(12) United States Patent
Strebelle et al.

(10) Patent No.: US 7,683,223 B2
(45) Date of Patent: Mar. 23, 2010

(54) METHOD FOR PURIFYING HYDROGEN CHLORIDE

(75) Inventors: Michel Strebelle, Brussels (BE); Michel Lempereur, Corbais (BE)

(73) Assignee: Solvay (Société Anonyme), Brussels (BE)

( * ) Notice: Subject to any disclaimer, the term of this patent is extended or adjusted under 35 U.S.C. 154(b) by 0 days.

(21) Appl. No.: 11/815,505

(22) PCT Filed: Feb. 6, 2006

(86) PCT No.: PCT/EP2006/050695

§ 371 (c)(1),
(2), (4) Date: Jul. 3, 2008

(87) PCT Pub. No.: WO2006/084832

PCT Pub. Date: Aug. 17, 2006

(65) Prior Publication Data

US 2009/0022653 A1     Jan. 22, 2009

(30) Foreign Application Priority Data

Feb. 8, 2005    (FR) ................................ 05 01249

(51) Int. Cl.
*C07C 17/156* (2006.01)
*B01D 53/14* (2006.01)

(52) U.S. Cl. ..................... 570/224; 95/187; 95/239; 96/243

(58) Field of Classification Search ............... 423/462, 423/481, 488, 245.1, 254.2, 502, 507; 422/4, 422/129; 95/149; 570/101, 216, 224
See application file for complete search history.

(56) References Cited

U.S. PATENT DOCUMENTS

| 3,411,867 A | | 11/1968 | Beech et al. |
| 3,618,295 A | * | 11/1971 | Geiger et al. .................. 95/182 |
| 4,935,220 A | | 6/1990 | Schneider et al. |
| 2004/0024244 A1 | | 2/2004 | Walsdorff et al. |
| 2004/0150123 A1 | | 8/2004 | Strofer et al. |
| 2004/0163411 A1 | | 8/2004 | Brady, Jr. et al. |
| 2006/0099138 A1 | * | 5/2006 | Walsdorff et al. ........... 423/502 |
| 2006/0123842 A1 | * | 6/2006 | Sohn et al. .................... 62/617 |
| 2007/0142682 A1 | | 6/2007 | Strebelle et al. |
| 2007/0161830 A1 | | 7/2007 | Strebelle |

FOREIGN PATENT DOCUMENTS

| CN | 1189787 | 8/1998 |
| DE | 1577 89 | 12/1982 |

(Continued)

OTHER PUBLICATIONS

ROEMPP Lexikon Online: "1, 2-Dichlorethan", Retrieved Form the Internet: URL:http://www.roempp.com, XP 002376355, 1994. (with English translation).

(Continued)

*Primary Examiner*—Wayne Langel
*Assistant Examiner*—Syed Iqbal
(74) *Attorney, Agent, or Firm*—Oblon, Spivak, McClelland, Maier & Neustadt, L.L.P.

(57) ABSTRACT

Method for purifying hydrogen chloride gas containing aromatic organic compounds, comprising at least one step of contacting the said hydrogen chloride with a scrubbing agent containing 1,2-dichlorethane.

19 Claims, 1 Drawing Sheet

FOREIGN PATENT DOCUMENTS

| | | |
|---|---|---|
| EP | 0 255 156 | 2/1988 |
| EP | 0 494 474 | 7/1992 |
| EP | 0 618 170 | 10/1994 |
| EP | 0 657 212 | 6/1995 |
| EP | 0 657 213 | 6/1995 |
| EP | 0 774 450 | 5/1997 |
| EP | 1 411 027 | 4/2004 |
| FR | 1 417 388 | 10/1965 |
| FR | 2 151 107 | 4/1973 |
| HU | 2002 03023 | 3/2004 |
| JP | 02 137704 | 5/1990 |
| PL | 136 598 | 3/1986 |
| PL | 162 910 | 1/1994 |
| WO | 96/39264 | 12/1996 |
| WO | 2004 056758 | 7/2004 |

OTHER PUBLICATIONS

Myszowski, et al., "Removal of Organic Compounds From Gaseous Hydrogen Chloride by an Absorption Method", Chemical Abstracts Service, Database Accession No. 107:157554, XP 002352445, 1986. (English abstract only).

Ullmann's Encyclopedia of Industrial Chemistry, Fifth, Completely Revised Edition, vol. B3, Unit Operations II, pp. 8-20-8-21 & 8-34-8-35, 1988.

U.S. Appl. No. 11/719,652, filed May 18, 2007, Strebelle, et al.

U.S. Appl. No. 11/914,048, filed Nov. 9, 2007, Strebelle, et al.

\* cited by examiner

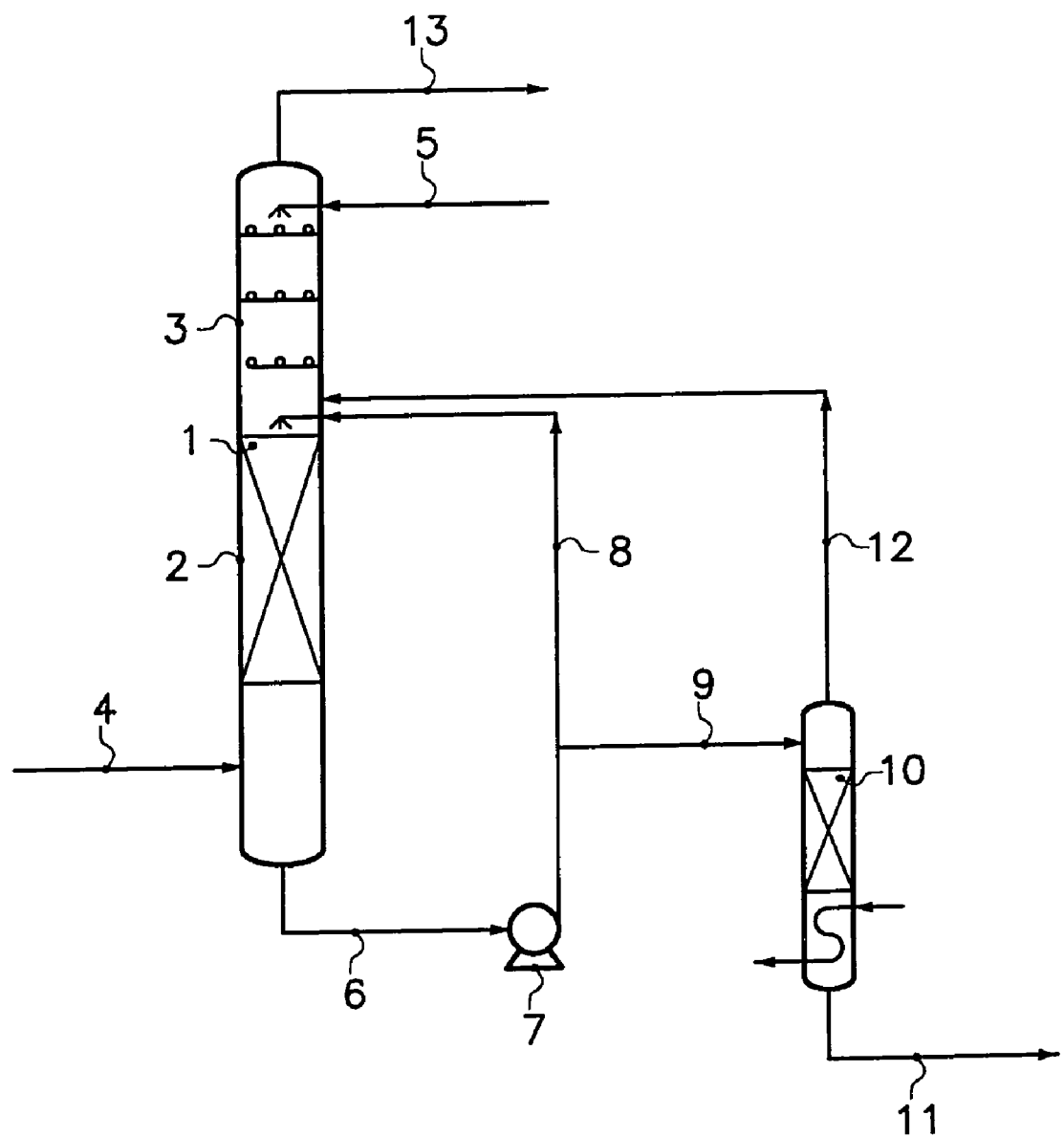

METHOD FOR PURIFYING HYDROGEN CHLORIDE

This application is a 371 of PCT/EP2006/050695 filed Feb. 6, 2006.

The present invention relates to a method for purifying hydrogen chloride. It relates more particularly to a method for purifying hydrogen chloride gas containing aromatic organic compounds, particularly chlorinated aromatic compounds. It further relates to an apparatus for purifying hydrogen chloride gas and to a method for ethylene oxychlorination using the hydrogen chloride obtained by the purification method according to the invention.

A large number of industrial chemical methods generate hydrogen chloride gas (HCl) as by-product. Among the most commonly practised, they include the production of vinyl chloride, the production of chloromethanes and chlorinated solvents of which the molecule contains two carbon atoms, the synthesis of isocyanates and the synthesis of fluorinated hydrocarbons.

This production of large quantities of HCl raises the problem of its purification when it is to be re-used as raw material for other methods.

Thus, concerning the production of vinyl chloride for example, the synthesis method by chlorination and oxychlorination of ethylene and thermal decomposition of the 1,2-dichlorethane (DCE) formed, would theoretically generate the quantity of HCL necessary for the method if it were reversible. In practice, however, it may be necessary to add make-up HCl from an external source. During the synthesis, to prevent the formation of toxic products and organic compounds detrimental to the effectiveness of the ethylene oxychlorination catalyst, it is important to use make-up HCl that has previously been purified. Thus document EP-A-774 450 teaches that the formation of polychlorinated dibenzodioxins (PCDD) and of polychlorinated dibenzofurans (PCDF) in oxychlorination can be ascribed to aromatic compounds which contaminate the reagents.

Methods for purifying HCl by scrubbing using solvents have already been described. Thus French patent 1 417 388 generally mentions the stripping of organic and inorganic matter from HCl by scrubbing using high boiling point organic compounds (page 4, left hand column, end of second paragraph); the French patent application published under number 2 151 107 refers (page 2, lines 18 to 31) to a method for extracting low boiling point impurities from hydrogen chloride by scrubbing with high boiling point perchlorinated hydrocarbons, and emphasises its drawbacks; the Japanese patent application published under number 02137704 A2 describes the purification of HCl containing chlorinated hydrocarbons by scrubbing with a pentachlorethane solution. The common drawback of all these purification methods is that the compound used for scrubbing contaminates the HCl in its turn, and the disposal of this compound raises a problem associated with the fact that HCl is still at least partially soluble in the liquid phase of the said compound.

According to document PL-B-162 910, HCl is separated from a mixture of non-aromatic organochlorine compounds in an absorber, with spraying with DCE cooled to between −25 and −15° C.

Document EP-A-0 774 450 mentions several "external" sources of make-up HCl useable for producing vinyl chlorides (page 3, lines 14 to 21). Amongst these sources figures the production of organic isocyanates. This document also describes several methods for removing the aromatic compounds from the "external" HCl to be used in an oxychlorination method (page 3, last 5 lines to page 4, line 17). These methods, which make use of fractional distillation including a condensation step, of adsorption or absorption by suitable liquids or solids, and of catalytic hydrogenation and oxidation reactions, all have drawbacks associated with the complexity of the apparatus to be used, with the need to regenerate the adsorbents or absorbents used, filled in their turn with the impurities present in the HCl to be purified, or with the need to regenerate the costly hydrogenation or oxidation catalysts used.

Document EP-A-0 618 170 discloses a method for obtaining pure "reagent grade" hydrochloric acid from the HCl produced during the production of organic isocyanates by reacting an organic amine with phosgene. For unclear reasons, this HCl often contains more than 200 ppb of iron-based impurities (EP-A-0 618 170, page 2, lines 27 to 37). The iron can catalyze side reactions like the addition of HCl to olefins or the formation of heavier compounds by alkylation of aromatics. The complicated and costly solution proposed in this document for removing these impurities is to convert this HCl to hydrochloric acid and then to contact this hydrochloric acid with an anion exchange resin.

Document US-A-2004/0163411 describes purification methods more particularly applicable to the HCl produced during the production of isocyanates. This HCl is soiled by chlorinated aromatic compounds, such as the chloro- and dichlorobenzene present in the isocyanate synthesis medium. The presence of these compounds, and of their conversion products, in the HCl used, for example, in the step of catalytic oxychlorination of ethylene to DCE, during the production of vinyl chloride, harms the progress of this oxychlorination step, particularly by deactivating the catalyst, irrespective of whether the catalyst bed is fluidized or fixed. The fixed bed is also sensitive to the accumulation of degradation or carbonation products which cause high pressure drops. To remedy this, it may become necessary to interrupt the production to renew all or part of the catalyst load. The solution proposed in document US-A-2004/0163411 for stripping the chlorinated aromatic compounds from HCl is a two-stage condensation with recycle of the colder condensed phase from the second stage to the first. This involves a complex device comprising a costly refrigeration unit requiring high energy consumption. Moreover, the efficiency of this stripping is limited by the vapour pressure of the aromatic compounds to be removed, at the temperature reached in condensation.

It is the object of the present invention to provide a method and an apparatus for purifying hydrogen chloride that does not have these drawbacks.

The present invention accordingly relates mainly to a method for purifying hydrogen chloride gas containing aromatic organic compounds, comprising at least one step of contacting the said hydrogen chloride with a scrubbing agent containing 1,2-dichlorethane.

In the present description, "scrubbing agent containing 1,2-dichlorethane" or simply "rubbing agent" means a composition in which 1,2-dichlorethane (DCE) is present in the liquid state.

The sole FIGURE of the drawing schematically shows a practical embodiment of the aspects of the invention.

The method according to the invention applies in general for purifying HCl produced by syntheses involving the presence of aromatic organic compounds. On account of this origin, this HCl contains, as impurities, one or more aromatic organic compounds of which the standard boiling point is generally above 100° C., compounds that are at least partially soluble in the scrubbing agent or miscible therewith. Preferably, the HCl to be purified is the by-product of the production of organic isocyanates by reacting phosgene with an organic amine, usually an aromatic amine and preferably an aromatic diamine. In this particular case, the impurities are frequently chloroaromatic compounds, typically chlorobenzene and dichlorobenzene, used as solvents in this production.

The scrubbing agent useable according to the present invention contains DCE in the liquid state. The presence, in the said scrubbing agent, of other compounds capable of solubilizing the impurity(ies) present in the HCl to be purified or of forming a liquid mixture with it (them) is not at all excluded from the framework of the invention. However, it is preferable for the scrubbing agent to contain at least 50% by volume of DCE, more particularly at least 80% by volume. In a particularly preferred manner, the scrubbing agent substantially consists of DCE in the liquid state, more precisely in the case in which the HCl to be purified is intended for re-use in a catalytic oxychlorination of ethylene to DCE. In this case, an essential advantage of the method of the invention resides in the fact that the presence of this DCE is not at all disturbing, because it is the main compound formed during this oxychlorination.

As stated above, if the HCl to be purified is the by-product of the production of organic isocyanates by reacting an organic amine with phosgene, it also generally contains iron-based impurities (cf. EP-A-0 618 170).

In general, the HCl contains metal impurities. These metal impurities include those resulting from corrosion of the installations, particularly those based on iron, nickel and chromium. Inorganic compounds entrained in the form of droplets or by vapour pressure, such as ammonium chloride, may also be present and disturbing in the downstream portion of the method, because they often promote clogging.

Unexpectedly, the purification method according to the invention is particularly simple and effective for removing metal impurities. Preferably, the purification method according to the invention is particularly simple and effective for removing iron-based impurities.

The various impurities may advantageously be present in the HCl gas in the state of droplets, solid particles or gas fractions.

The method according to the invention is advantageously implemented at any pressure compatible with the maintenance of the HCl to be purified in the gas state. This pressure is generally between 1 and 20 bar, preferably between 5 and 15 bar, more particularly about 10 bar. The temperature at which the method is implemented could easily be selected by a person skilled in the art in order to promote the dissolution and/or absorption of the impurities in the scrubbing agent and taking account of the vapour pressure of the aromatic organic compounds present as impurities in the HCl to be purified. This temperature is generally between −20 and +50° C., preferably between 0 and +35° C. Values close to ambient temperature (about 25° C.) are particularly preferred.

The ratio of the respective of scrubbing agent and of HCl flow rates to be purified is not critical and may vary greatly. It is only limited in practice by the cost of regenerating the scrubbing agent. In general, the flow rate of scrubbing agent is between 0.5 and 50% by weight with respect to the flow rate of HCl to be purified, preferably between 1 and 20%, and particularly between 2 and 10%.

The method according to the invention can be carried out in continuous or batch mode. Continuous mode is preferred.

The method according to the invention comprises at least one step of contacting the HCl with the scrubbing agent. Preferably, and in the case of continuous operation, it is nevertheless carried out in two steps; one of the steps comprising loop flow (recycle) of the scrubbing agent and the other step comprising an addition of make-up fresh scrubbing agent. In this case, the flow rate of fresh scrubbing agent is generally between 0.1 and 10% by weight of the flow rate of HCl to be purified, preferably between 0.5 and 5%, and particularly about 2.5%.

The liquid mixture or solution (called fraction (f) below) comprising the scrubbing agent, containing the impurities extracted from the HCl to be purified, and also the part of this HCl that is dissolved in or mixed with the said scrubbing agent, can then be treated, at least partly, by any known means, to separate the HCl therefrom, for example by scrubbing, neutralization, settling, distillation, absorption, stripping, etc.

It is preferable to separate the HCl from the scrubbing agent containing impurities by subjecting all or at least part of the fraction (f) to a stripping operation. Preferably, only part of the fraction (f) is stripped. For this purpose, the fraction (f) is advantageously divided into a liquid fraction (f1) and a liquid fraction (f2). This division can be effected using any known device for splitting a liquid stream into two and for regulating the resulting flow rates, such as a tee fitted with flow control valves, for example. In the case in which the purification method according to the invention is carried out in continuous mode, the fraction (f1), enriched with scrubbing agent, is advantageously recycled to the step of contacting the HCl with the scrubbing agent. The fraction (f2) (also called the "purge stream") is advantageously subjected to the stripping operation mentioned above, during which the HCl present in this fraction (f2)—which may be recycled to the contacting step with the scrubbing agent—is separated from the remainder of the purge stream essentially comprising the residual scrubbing agent containing impurities.

In the particularly preferred case, mentioned above, in which the stripping agent substantially consists of DCE in the liquid state, this residual purge stream can be utilised advantageously by sending it to a unit in which, in a first variant, the scrubbing, neutralization and/or settling of the DCE resulting from an ethylene oxychlorination step to which the purge stream may be added, is carried out in one or more steps. The DCE is then advantageously dried and distilled before use. In a second variant, the residual purge stream can be sent directly to the distillation step which precedes its use without being subjected to prior scrubbing, neutralization, settling and/or drying. However, the first variant is preferred. The DCE obtained can be used for any purpose, but is preferably pyrolyzed to produce vinyl chloride.

The respective proportions of liquid fractions (f1) and (f2), resulting from the splitting of the fraction (f), may vary greatly. The flow rate of fraction (f2) is generally selected so as to limit the energy consumption required by the stripping operation and to sufficiently strip the fraction (f1) of impurities to ensure proper purification of the HCl. The flow rate of the fraction (f2) is generally between 1 and 70% by weight of the flow rate of the fraction (f), preferably between 10 and 50% by weight, more particularly between 15 and 35% by weight.

The purification method according to the invention is highly efficient. This method serves to reduce the level of aromatic organic impurities to below 100 ppm, preferably to below 50 ppm. In the case of the chloroaromatic compounds mentioned above, the method according to the invention can be used to obtain a residual content of not more than 10 ppm in the HCl. As to the metal impurities, particularly the iron-based impurities mentioned above, the purification method according to the invention serves to reduce their level to below 5 ppm, preferably to below 0.5 ppm. In a particularly preferred manner, thanks to the method according to the invention, the residual content of metal impurities, particularly iron, in the HCl, does not exceed 200 ppb.

The method according to the invention has the advantage of avoiding the formation of toxic products such as PCDD and PCDF by sending aromatic compounds to oxychlorination. It also has the advantage of preventing clogging by the deposition of inorganic elements and also side reactions to oxychlorination caused by the introduction of iron-based contaminants.

According to another aspect, the invention further relates to an apparatus for purifying HCl gas. This apparatus comprises at least one scrubber with countercurrent flow of the HCl to be purified and of the scrubbing agent defined above, the said scrubber comprising two sections placed one above the other. The purified HCl gas escapes at the top of the column. At the base of the column, a fraction (f) is collected comprising the scrubbing agent, the impurities (as defined above) extracted from the HCl to be purified and the portion of this HCl that is dissolved or mixed with the scrubbing agent.

In the scrubber comprising two sections, the first section is advantageously supplied with at least part of the fraction (f) defined above, tapped off at the base of this section and recycled in loop mode. This fraction (f) can advantageously be treated, during its recycling, fully or partially, by any known means for this purpose, in order to separate the scrubbing agent containing the impurities that it has extracted from the HCl. These means may be those mentioned above concerning the treatment of the fraction (f). The fraction (f) is preferably treated, at least partly, in a stripper, to extract the impurities therefrom, before being recycled to the top of the first section of the scrubber.

In the scrubber comprising two sections, the second section, placed above the first, is advantageously supplied with fresh scrubbing agent.

The scrubber may be equipped with any known type of packing material that promotes exchanges between the component in the gas state to be purified (HCl) and the liquid scrubbing agent. A description of the most commonly used materials is given, for example, in sections 3.4, 3.5 and 3.6 of pages 8-20 and 8-21 of volume B 3: Unit Operations II of Ullmann's Encyclopedia of Industrial Chemistry, Fifth, Completely Revised Edition, published by VCH, 1988. In the scrubber comprising two sections, a packing consisting of Raschig rings or Berl saddles has been found to be advantageous, with a particular preference for Berl saddles, in the first section, because of the often high liquid flow rate passing through this section. The second section, which only receives make-up scrubbing agent, can advantageously be provided with bubble cap trays for good contact of the liquid and gas phases.

The invention finally relates to a method for ethylene oxychlorination into 1,2-dichloroethane using the hydrogen chloride obtained by the purification method according to the invention.

The oxychlorination reaction is advantageously performed in the presence of a catalyst comprising active elements including copper deposited on an inert support. The inert support is advantageously chosen from alumina, silica gels, mixed oxides, clays and other supports of natural origin. Alumina constitutes a preferred inert support.

Catalysts comprising active elements which are advantageously at least two in number, one of which is copper, are preferred. Among the active elements other than copper, there may be mentioned alkali metals, alkaline-earth metals, rare-earth metals and metals of the group consisting of ruthenium, rhodium, palladium, osmium, iridium, platinum and gold. The catalysts containing the following active elements are particularly advantageous: copper/magnesium/potassium, copper/magnesium/sodium; copper/magnesium/lithium, copper/magnesium/caesium, copper/magnesium/sodium/lithium, copper/magnesium/potassium/lithium and copper/magnesium/caesium/lithium, copper/magnesium/sodium/potassium, copper/magnesium/sodium/caesium and copper/magnesium/potassium/caesium. The catalysts described in patent applications EP-A 255 156, EP-A 494 474, EP-A-657 212 and EP-A 657 213, incorporated by reference, are most particularly preferred.

The copper content, calculated in metal form, is advantageously between 30 and 90 g/kg, preferably between 40 and 80 g/kg and in a particularly preferred manner between 50 and 70 g/kg of catalyst.

The magnesium content, calculated in metal form, is advantageously between 10 and 30 g/kg, preferably between 12 and 25 g/kg and in a particularly preferred manner between 15 and 20 g/kg of catalyst.

The alkali metal content, calculated in metal form, is advantageously between 0.1 and 30 g/kg, preferably between 0.5 and 20 g/kg and in a particularly preferred manner between 1 and 15 g/kg of catalyst.

The Cu:Mg:alkali metal(s) atomic ratios are advantageously 1:0.1-2:0.05-2, preferably 1:0.2-1.5:0.1-1.5 and in a particularly preferred manner 1:0.5-1:0.15-1.

Catalysts having a specific surface area, measured according to the B.E.T. method with nitrogen, advantageously between 25 m²/g and 300 m²/g, preferably between 50 and 200 m²/g and in a particularly preferred manner between 75 and 175 m²/g, are particularly advantageous.

The catalyst may be used in a fixed bed or in a fluidized bed. This second option is preferred. The oxychlorination process is advantageously exploited under the range of the conditions usually recommended for this reaction. The temperature is advantageously between 150 and 300° C., preferably between 200 and 275° C. and most preferably from 215 to 255° C. The pressure is advantageously greater than atmospheric pressure. Values of between 2 and 10 absolute bar gave good results. The range between 4 and 7 absolute bar is preferred. This pressure may be usefully modulated in order to obtain an optimum residence time in the reactor and to maintain a constant rate of passage for various speeds of operation. The usual residence times range from 1 to 60 seconds and preferably from 10 to 40 seconds.

The source of oxygen for this oxychlorination may be air, pure oxygen or a mixture thereof, preferably pure oxygen. The latter solution, which allows easy recycling of the unconverted reagents, is preferred.

The reagents may be introduced into the bed by any known device. It is generally advantageous to introduce the oxygen separately from the other reagents for safety reasons. These also require maintaining the gaseous mixture leaving the reactor or recycled thereto outside the limits of inflammability at the pressures and temperatures considered. It is preferable to maintain a so-called rich mixture, that is containing too little oxygen relative to the fuel to ignite. In this regard, the abundant presence (>2%, preferably >5% vol) of hydrogen would constitute a disadvantage given the wide range of inflammability of this compound.

The hydrogen chloride (HCl)/oxygen ratio used is advantageously between 3 and 6 mol/mol. The ethylene/hydrogen chloride ratio is advantageously between 0.4 and 0.6 mol/mol.

The DCE obtained by oxychlorination of ethylene may then be subjected to a pyrolysis into vinyl chloride which may then be polymerized into polyvinyl chloride.

The purification method and apparatus according to the invention will now be illustrated with reference to the drawing appended to the present description. This drawing consists of the sole FIGURE appended hereto, schematically showing a practical embodiment of the aspects of the invention. According to this embodiment, the HCl gas issues from an isocyanate production unit and is soiled by impurities essentially consisting of monochlorobenzene at the rate of 250 ppm and iron at the rate of 10 ppm. The scrubbing agent consists of DCE. The purified HCl is sent to an ethylene oxychlorination unit.

The HCl to be purified is introduced via the line 4 into the section 2 of the scrubber 1 where the temperature is 25° C. and the pressure is 10 bar. Fresh DCE (necessary for make-up, because of the entrainment by vapour pressure of DCE to the ethylene oxychlorination unit via the purified HCl and the removal of DCE via the purge system (see below)) is introduced at a flow rate representing about 2.5% by weight of the flow rate of HCl to be purified, via the line 5 into the section 3 of the scrubber 1. The section 2 of the scrubber 1 is packed with Berl saddles. The section 3 of the scrubber 1 is provided with bubble cap trays. A liquid fraction (f) comprising DCE containing the dissolved impurities extracted from the HCl to be purified and part of this HCl is tapped off at the bottom of the column 1 via the line 6 and recycled in loop mode to the top of the section 2 via the pump 7 and the line 8 with a flow rate representing about 7% by weight of the flow rate of HCl to be purified. The system for purging DCE contaminated by monochlorobenzene and iron comprises a stripping and separation column 10 supplied, via the line 9, with a liquid fraction (f2), bypassed from the fraction (f). The flow rate of the fraction (f2) represents 25% by weight of the flow rate of the fraction (f) from which it is bypassed. The stripping column sends most of the dissolved HCl to the scrubber 1 via the line 12. The residual purge stream removed via the line 11 essentially contains DCE containing monochlorobenzene and iron. Its flow rate only represents 0.2% by weight of the flow rate of HCl to be purified and it can be treated easily by the scrubbing, neutralization and/or settling systems immediately following the oxychlorination reactor at the same time as the DCE synthesized in the oxychlorination reactor. The DCE can then be dried and distilled before use. The purified HCl gas leaves the column 1 via the line 13 and is sent to the ethylene oxychlorination unit.

Thanks to this apparatus, the monochlorobenzene content of the HCl is reduced from 250 ppm to below 10 ppm in the liquid fraction leaving the column 1 via the line 13. The inorganic contamination is also reduced: the iron content of the gas phase drops from 10 ppm to below 200 ppb. Hence this operation serves effectively to purify the HCl of chlorobenzene and to remove the iron therefrom, whether the latter is present in the form of solid particles, droplets or a gas fraction. A product useable without any problem for an ethylene oxychlorination step is thus obtained.

The invention claimed is:

1. A method for purifying hydrogen chloride gas containing one or more aromatic organic compounds, comprising contacting said hydrogen chloride gas with a scrubbing agent comprising 1,2-dichloroethane.

2. The method according to claim 1, in which the hydrogen chloride gas is the by-product of the reaction of phosgene with an organic amine in the production of organic isocyanates.

3. The method according to claim 1, in which the hydrogen chloride gas comprises at least one chloroaromatic compound.

4. The method according to claim 1 in which the hydrogen chloride gas further comprises at least one metal impurity.

5. The method according to claim 1, in which the scrubbing agent consists essentially of 1,2-dichloroethane in the liquid state.

6. The method according to claim 1, in which the contacting of the HCl gas with the scrubbing agent is carried out at temperature of between −20 and +50° C.

7. The method according to claim 1, in which the contacting of the HCl gas with the scrubbing agent is carried out at a pressure of between 1 and 20 bar.

8. The method according to claim 1, in which a flow rate of scrubbing agent is between 0.5 and 50% by weight of a flow rate of HCl gas to be purified.

9. The method according to claim 1, further comprising, after said contacting, obtaining purified hydrogen chloride gas and then providing the purified hydrogen chloride gas as a reactant to an ethylene oxychlorination reaction.

10. The method of claim 9, wherein said ethylene oxychlorination reaction is a reaction converting ethylene into 1,2-dichloroethane in the presence of a catalyst comprising copper on an inert support.

11. The method according to claim 1, in which the contacting produces a liquid mixture comprising the scrubbing agent, impurities extracted from the HCl gas, and HCl.

12. The method according to claim 11, further comprising stripping HCl from only a part of the liquid mixture to provide a fraction (f1), enriched with scrubbing agent, which is recycled to contact said hydrogen chloride gas containing one or more aromatic organic compounds.

13. The method according to claim 1, wherein said method reduces the level of aromatic organic impurities in said hydrogen chloride gas to below 100 ppm.

14. The method according to claim 1, wherein said method reduces the level of chloroaromatic compounds in said hydrogen chloride gas to below 10 ppm.

15. The method according to claim 1, wherein said method reduces the level of metal impurities in said hydrogen chloride gas to below 5 ppm.

16. The method according to claim 1, wherein said method reduces the level of iron in said hydrogen chloride gas to 200 ppb or less.

17. The method according to claim 3, in which the hydrogen chloride gas comprises at least one chloroaromatic compound selected from the group consisting of chlorobenzene and dichlorobenzene.

18. The method according to claim 1, in which the scrubbing agent comprises at least 50% by volume of 1,2-dichloroethane.

19. The method according to claim 1, in which the scrubbing agent comprises at least 80% by volume of 1,2-dichloroethane.

* * * * *